United States Patent
Williams et al.

(10) Patent No.: US 11,771,906 B2
(45) Date of Patent: Oct. 3, 2023

(54) TEMPORARY PACEMAKER

(71) Applicant: Cardiac Pacemakers, Inc., St Paul, MN (US)

(72) Inventors: Thomas Lee Williams, Blaine, MN (US); James Michael English, Cahir (IE); Geordie T. Alfson, Blaine, MN (US); Bryan Peter Nelson, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 274 days.

(21) Appl. No.: 17/122,480

(22) Filed: Dec. 15, 2020

(65) Prior Publication Data

US 2021/0213284 A1   Jul. 15, 2021

Related U.S. Application Data

(60) Provisional application No. 62/958,843, filed on Jan. 9, 2020.

(51) Int. Cl.
*A61N 1/362* (2006.01)
*A61N 1/378* (2006.01)
*A61N 1/375* (2006.01)

(52) U.S. Cl.
CPC .................. *A61N 1/3625* (2013.01)

(58) Field of Classification Search
CPC .............. A61N 1/3625; A61N 1/37512; A61N 1/3572; A61N 1/3758; A61N 1/378
See application file for complete search history.

(56) References Cited

U.S. PATENT DOCUMENTS

| | | |
|---|---|---|
| 3,807,411 A | 4/1974 | Concept |
| 5,050,600 A | 9/1991 | Parks |
| 5,304,209 A | 4/1994 | Adams et al. |
| 9,802,051 B2 | 10/2017 | Mathur et al. |
| 2013/0245710 A1* | 9/2013 | Foster .................. A61N 1/3752 607/37 |
| 2014/0364869 A1 | 12/2014 | Ranu |
| 2015/0100106 A1* | 4/2015 | Shishilla .............. A61N 1/3615 607/2 |
| 2015/0238770 A1 | 8/2015 | Dorman et al. |
| 2016/0045745 A1 | 2/2016 | Mathur et al. |
| 2016/0067502 A1 | 3/2016 | Bornzin et al. |

(Continued)

FOREIGN PATENT DOCUMENTS

| | | |
|---|---|---|
| EP | 0551708 A1 | 7/1993 |
| EP | 3180071 A1 | 6/2017 |

(Continued)

OTHER PUBLICATIONS

International Search Report and Written Opinion received for PCT Patent Application No. PCT/US20/65088, dated Mar. 16, 2021, 11 pages.

*Primary Examiner* — Brian T Gedeon
(74) *Attorney, Agent, or Firm* — Nelson Mullins Riley & Scarborough

(57) ABSTRACT

A disposable pacemaker comprises a housing including a stylet port, a pulse generator printed circuit board assembly situated in the housing, and a pacing lead secured to the housing. The pacing lead includes a lumen aligned with the stylet port, such that the stylet port and the lumen of the pacing lead are configured to receive a stylet.

17 Claims, 7 Drawing Sheets

(56) References Cited

U.S. PATENT DOCUMENTS

2017/0182326 A1  6/2017  Bornzin et al.
2018/0117344 A1  5/2018  Mathur et al.

FOREIGN PATENT DOCUMENTS

| EP | 3375483 A1 | 9/2018 | |
|---|---|---|---|
| GB | 2277269 A | 10/1994 | |
| WO | 2016/025909 A1 | 2/2016 | |
| WO | WO-2016026914 A2 * | 2/2016 | ........... A61N 1/0524 |
| WO | 2017/081341 A1 | 5/2017 | |

* cited by examiner

TEMPORARY PACEMAKER

CROSS REFERENCE TO RELATED APPLICATION

This application claims priority to Provisional Application No. 62/958,843, filed Jan. 9, 2020, which is herein incorporated by reference in its entirety.

TECHNICAL FIELD

The present disclosure relates to medical devices, such as pacemakers, and related methods. More specifically, the present disclosure relates to disposable temporary pacemakers.

BACKGROUND

Sometimes, cardiac patients are stabilized using a temporary pacing system prior to the patient having a pacemaker implanted. This may occur at a medical facility that performs pacemaker implantation procedures, where a patient is stabilized before an operation is performed at the facility, or this may occur at a medical facility that does not perform pacemaker implantation procedures, where a patient in need of a pacemaker is admitted to the facility and the patient is stabilized before being transported to a medical center that implants pacemakers.

Current temporary pacing systems include a capital equipment box that is connected to the heart through a set of wires and connectors that interface to custom cardiac leads. However, the capital equipment box is bulky, such that the mobility of the patient is limited while the patient is under temporary pacing therapy, and the patient is at risk of becoming entangled in the wires leading to the capital box. Also, the capital equipment box is expensive and turn-around time for maintenance of the capital equipment box may be longer than practical. In addition, some medical facilities may not have access to a temporary pacing system.

SUMMARY

In Example 1, a disposable pacemaker, comprising a housing including a stylet port, a pulse generator printed circuit board assembly situated in the housing, and a pacing lead secured to the housing. The pacing lead includes a lumen aligned with the stylet port, such that the stylet port and the lumen of the pacing lead are configured to receive a stylet.

In Example 2, the disposable pacemaker of Example 1, wherein the pacing lead is immovably secured to the housing.

In Example 3, the disposable pacemaker of Example 1, wherein the pacing lead is removably secured to the housing.

In Example 4, the disposable pacemaker of any of Examples 1-3, wherein the pulse generator printed circuit board assembly includes a first pulse generator contact and a second pulse generator contact, and wherein the pacing lead includes a first pacing lead contact electrically coupled to the first pulse generator contact, and a second pacing lead contact electrically coupled to the second pulse generator contact.

In Example 5, the disposable pacemaker of any of Examples 1-4, wherein the housing includes a first portion and a second portion secured together to form the housing.

In Example 6, the disposable pacemaker of Example 5, wherein the first portion and the second portion are secured together by at least one of an interference fit or an adhesive and the pacing lead is irremovably secured to the first portion of the housing.

In Example 7, the disposable pacemaker of either of Examples 5 or 6, wherein the pulse generator printed circuit board assembly includes electronics that face the second portion and the pulse generator printed circuit board assembly is sealed into the second portion to protect the electronics from an external environment.

In Example 8, the disposable pacemaker of any of Examples 5-7, wherein the first portion includes the stylet port.

In Example 9, the disposable pacemaker of any of Examples 4-8, wherein the each of the first and second pulse generator contacts and the first and second pacing lead contacts, respectively, are pressed together to make electrical contact with each other.

In Example 10, the disposable pacemaker of any of Examples 1-9, wherein the pulse generator printed circuit board assembly includes a battery.

In Example 11, the disposable pacemaker of any of Examples 5-10, wherein the pulse generator printed circuit board assembly includes a circuit board and pacing electronics on the circuit board that face the second portion and comprising a seal formed between or around the circuit board and the second portion.

In Example 12, the disposable pacemaker of any of Examples 5-11, wherein the pacing lead is irremovably secured to the first portion of the housing.

In Example 13, the disposable pacemaker of either of Examples 11 or 12, wherein the pulse generator printed circuit board assembly includes a battery held on the circuit board, and further comprising a power pull-tab situated between the battery and the circuit board, the power pull-tab being removable therefrom to electrically connect the battery and the circuit board.

In Example 14, the disposable pacemaker of Example 13, further comprising an expandable pad situated between the housing and the power pull-tab, wherein the expandable pad expands to protect an inside of the housing after the power pull-tab has been removed.

In Example 15, the disposable pacemaker of any of Examples 1-14, wherein the housing is non-conductive and is formed from a polymeric material.

In Example 16, a disposable pacemaker, comprising a non-conductive housing, a pulse generator printed circuit board assembly, and a pacing lead. The housing is non-conductive and is formed of a polymeric material. The pulse generator printed circuit board assembly is situated in the housing. The pacing lead is irremovably secured to the housing and includes first and second electrodes each electrically coupled to the pulse generator circuit board assembly and configured to deliver pacing pulses generated by the pulse generator circuit board assembly.

In Example 17, the disposable pacemaker of Example 16, wherein the housing includes a first portion and a second portion secured together to form the housing.

In Example 18, the disposable pacemaker of Example 17, wherein the first portion and the second portion are secured together by at least one of an interference fit, an adhesive, or latches.

In Example 19, the disposable pacemaker of Example 17, wherein the pacing lead is irremovably secured to the first portion of the housing.

In Example 20, the disposable pacemaker of Example 17, wherein the pulse generator printed circuit board assembly includes electronics that face the second portion, and the pulse generator printed circuit board assembly and the second portion are sealed together to protect the electronics from an external environment.

In Example 21, the disposable pacemaker of Example 17, wherein the first portion includes a stylet port and the pacing lead includes a lumen aligned with the stylet port, such that the stylet port and the lumen of the pacing lead are configured to receive a stylet.

In Example 22, the disposable pacemaker of Example 16, wherein the pulse generator printed circuit board assembly includes a first pulse generator contact and a second pulse generator contact, and the pacing lead includes a first pacing lead contact electrically coupled to the first electrode and to the first pulse generator contact, and a second pacing lead contact electrically coupled to the second electrode and the second pulse generator contact.

In Example 23, the disposable pacemaker of Example 16, wherein the pulse generator printed circuit board assembly includes a battery and pacing electronics, and further comprising power pull-tab removably disposed between the battery and the pacing electronics to selectively electrically isolate the battery and the pacing electronics.

In Example 24, a disposable pacemaker comprising a housing, a pulse generator printed circuit board, and a pacing lead. The housing includes a first portion having a stylet port and a second portion. The pulse generator printed circuit board assembly is situated between the first portion and the second portion and including at least a first pulse generator contact and a second pulse generator contact. The pacing lead is secured into the first portion, wherein the pacing lead has a first pacing lead contact configured to make electrical contact with the first pulse generator contact, and a second pacing lead contact configured to make electrical contact with the second pulse generator contact, the pacing lead further including a lumen aligned with the stylet port.

In Example 25, the disposable pacemaker of Example 24, wherein the stylet port and the lumen of the pacing lead are configured to receive a stylet.

In Example 26, the disposable pacemaker of Example 24, wherein the first portion and the second portion are secured together by at least one of an interference fit, an adhesive, or one or more latches.

In Example 27, the disposable pacemaker of Example 24, wherein the pulse generator printed circuit board assembly includes a circuit board and pacing electronics on the circuit board that face the second portion and comprising a seal formed between or around the circuit board and the second portion.

In Example 28, the disposable pacemaker of Example 24, wherein the pacing lead is permanently secured to the first portion of the housing.

In Example 29, the disposable pacemaker of Example 24, wherein the pulse generator printed circuit board assembly includes a battery disposed on a circuit board.

In Example 30, the disposable pacemaker of Example 29, wherein the battery is secured onto the circuit board, such that a power pull-tab is removably situated between the battery and the circuit board to selectively electrically isolate the battery from the circuit board.

In Example 31, a pacemaker kit comprising a disposable pacemaker, a stylet and a power pull-tab. The disposable pacemaker includes a housing having a stylet port, a pulse generator printed circuit board assembly situated in the housing, and a pacing lead secured to the housing. The housing has a stylet port. The pulse generator printed circuit board assembly includes pacing electronics attached to a circuit board and a battery held on the circuit board, and the pacing lead includes a lumen aligned with the stylet port and is in electrical contact with the pacing electronics. The stylet is configured to be inserted into the stylet port and the lumen of the pacing lead. The power pull-tab is removably positioned between the battery and the circuit board to electrically isolate the battery from the circuit board, wherein removal of the power pull-tab electrically couples the battery and the circuit board to enable the pulse generator printed circuit board assembly to generate electrical pacing pulses.

In Example 32, the pacemaker kit of Example 31, wherein the housing includes a first portion and a second portion secured together to form the housing.

In Example 33, the pacemaker kit of Example 32, wherein the pacing lead is irremovably secured to the first portion.

In Example 34, the pacemaker kit of Example 32, wherein the circuit board is situated in the second portion with the pacing electronics facing the second portion and comprising a seal formed between or around the circuit board and the second portion to protect the pacing electronics from an external environment.

In Example 35, the pacemaker kit of Example 31, comprising an expandable pad situated between the housing and the power pull-tab, wherein the expandable pad expands to protect the inside of the housing upon removal of the power pull-tab from between the battery and the circuit board.

While multiple embodiments are disclosed, still other embodiments of the present disclosure will become apparent to those skilled in the art from the following detailed description, which shows and describes illustrative embodiments of the disclosure. Accordingly, the drawings and detailed description are to be regarded as illustrative in nature and not restrictive.

Figure 1:
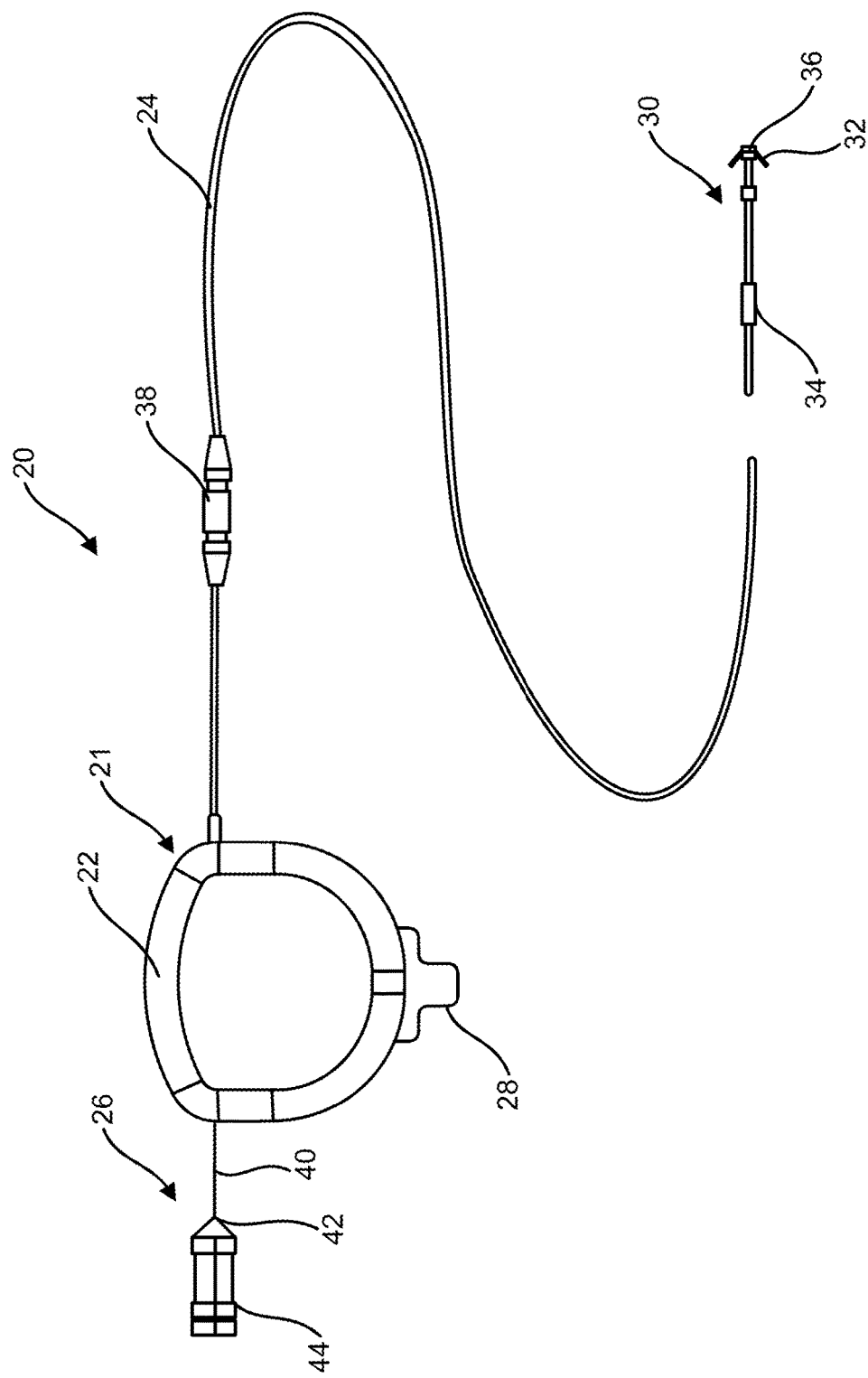
FIG. 1 is a diagram illustrating a disposable temporary pacemaker system, according to embodiments of the disclosure.

While the disclosure is amenable to various modifications and alternative forms, specific embodiments have been shown by way of example in the drawings and are described in detail below. The intention, however, is not to limit the disclosure to the particular embodiments described. On the contrary, the disclosure is intended to cover all modifica-

DETAILED DESCRIPTION

This disclosure is directed to an integrated, single use, disposable temporary pacemaker system that includes a pulse generator (PG), one or more attached leads, and lead delivery capabilities. The disposable temporary pacemaker system differs from an implantable pacemaker and lead system, in that the PG portion of the disposable temporary pacemaker is not implanted. In addition, the one or more attached leads of the disposable temporary pacemaker would likely be introduced through the jugular vein (endocardial) or through a post-operative chest incision (epicardial) rather than through the subclavian access of a permanent pacemaker.

In the disposable temporary pacemaker system, the PG remains outside the patient's body, such that it can be bandaged to the patient's body, while each of the leads passes into the body and is connected to the heart. This arrangement allows the patient to be both mobile and eliminates the risk of entanglement with the pacing wires of a capital box.

The construction of the disposable temporary pacemaker system is such that the cost is lower than either a classic pacemaker or a capital box solution, allowing it to be single use and disposable. This is achieved through employing an inexpensive housing for the PG, a low-cost chip set for the PG, and an off-the-shelf commercially available battery. In addition, the cost of cardiac leads can be minimized through the elimination of the need for a sealed IS1 standard proximal end connection to the PG.

Thus, the current disclosure is directed to a disposable temporary pacemaker that does not limit the mobility of the patient and that has a smaller number and/or shorter lengths of wires, which lowers the risk of the patient becoming entangled in the wires. Also, the disposable temporary pacemaker is a low-cost item that requires little or no maintenance. In addition, due to its low-cost and ease of use, the disposable temporary pacemaker can be made available at virtually every medical facility.

The disposable temporary pacemaker system can be used for a wide range of medical conditions, from simple bradycardia to complex idioventricular rhythms. And the disposable temporary pacemaker can be used in transcatheter aortic valve replacement (TAVR) procedures, which employ temporary pacemakers during the implant procedure.

FIG. 1 is a diagram illustrating a disposable temporary pacemaker system 20 including a PG 21 including a pacemaker body or housing 22, a pacing lead 24, a guide wire or stylet 26, and a power pull-tab 28. FIGS. 2, 3, 4A-4B and 5A-5B are perspective and side views of portions of the housing 22 and other components of the temporary pacemaker system 20 as described in detail herein. As such, the following description is in reference to FIGS. 1, 2, 3, 4A-4B and 5A-5B, individually and collectively.

In the illustrated embodiment, the pacemaker system 20 includes a single lead 24 and a single stylet 26 associated therewith. However, in other embodiments, the pacemaker system 20 may include multiple leads so as to provide the capability for atrioventricular (AV) pacing. For example, the pacemaker system 20 could include a first lead sized and otherwise configured for being positioned within the right atrium, and a second lead configured to be positioned in the right ventricle. In such embodiments, the pacemaker system 20 may include more than one stylet 26, e.g., one associated with each lead, or alternatively, a single stylet 26 may be used (i.e., is removed after delivery of one lead and used for delivery of the second lead).

The housing 22 contains a PG assembly (not shown in FIG. 1) that includes pacing circuitry or pacing electronics that generate electrical pulses for pacing the heart, a pacing lead interface that includes one or more pulse generator contacts for electrically coupling the PG assembly to the pacing lead 24, and a battery configured to power the pacing electronics. The housing 22 further includes a stylet access port that is aligned with a lumen of the pacing lead 24. In some embodiments, the PG assembly is similar to PG printed circuit board assembly 48 (shown in FIGS. 2, 3, 5A, and 5B) that includes a printed circuit board 70 having pacing electronics 72 on one side of the printed circuit board 70 and pulse generator contacts 74 and 76, a battery 78, and a battery holder 84 on the other side of the printed circuit board 70.

The pacing electronics that may be similar to pacing electronics 72 can be configured to provide pacing for a wide range of medical conditions, from simple bradycardia to complex idioventricular rhythms. In embodiments, the pacing electronics is configured to provide industry standard pacing modes. In embodiments, the pacing electronics is configured to provide anti-tachycardia pacing. In embodiments, the pacing electronics can be used in pacing for TAVR procedures. In embodiments, the pacing electronics are externally configured and/or programmed to provide the proper pacing.

The catheter pacing lead 24 has a proximal end situated inside the housing 22 and the pacing lead 24 is physically secured to the housing 22 inside the housing 22. In one embodiment, the pacing lead 24 is permanently, physically secured to the housing 22 inside the housing 22. In some embodiments, the pacing lead 24 is irremovably, physically secured to the housing 22 inside the housing 22. In such embodiments, the pacing lead 24 can be secured to the housing 22 via an adhesive or epoxy material, by mechanical connection means, or by an alternative connection means. The foregoing embodiments can operate to simplify the clinical procedure in which the system 20 is used, e.g., by providing a pre-assembled temporary pacemaker device that requires minimal preparation by the clinician prior to use (that is, the user can simply remove the permanently pre-assembled housing 22 and pacing lead 24 assembly from the packaging and continue on with the clinical procedure).

In other embodiments, however, the housing 22 and the pacing lead 24 may be configured such that the pacing lead 24 can be releasably operatively coupled to the housing 22, either prior to packaging or in the operating environment. In embodiments, the pacing lead 24 can be configured to be inserted into a port in the housing 22 by the user, e.g., with a snap-fit or similar connection approach, and thereafter removed from the housing 22 if desired. By way of example only, and without in any way limiting the present disclosure, the housing 22 can be packaged together with two pacing leads 24 (e.g., one configured for atrial stimulation and the other for ventricular stimulation) that are not pre-assembled to the housing 22, and the user can select whichever pacing lead 24 is most appropriate for the particular clinical procedure being performed.

The pacing lead 24 further includes one or more pacing lead contacts situated inside the housing 22 and used to electrically couple the pacing lead 24 to the PG assembly, such as to PG printed circuit board assembly 48. Also, the pacing lead 24 includes pacing electrodes 34 and 36 electrically coupled to the one or more pacing lead contacts. In the illustrated embodiment, the pacing electrode 34 is a ring electrode that is proximal a distal end 30 of the pacing lead 24, and the pacing electrode 36 is a tip electrode situated at the tip of the distal end 30. The distal end 30 of the pacing lead 24 is configured to be inserted into the patient's heart and the pacing lead 24 includes an anchoring system 32 situated at the distal end 30 of the pacing lead 24. The anchoring system 32 is configured to anchor or stabilize the pacing lead 24 in the patient's heart. In embodiments, the pacing lead 24 further includes items such as a suture sleeve 38 for holding or securing the catheter pacing lead 24 in place.

In other embodiments, the pacing lead 24 can include more than two pacing electrodes. For example, in one embodiment (not shown), the pacing lead 24 may include an additional, proximal electrode located on the pacing lead 24 so as to be positioned within the patient's right atrium when the pacing electrode 36 is located within the right ventricle, thus providing the capability of delivering pacing pulses from the tip electrode 36 to the right atrial electrode.

The stylet 26 includes a stylet wire 40 that has a proximal end 42 attached to a stylet handle 44 and a distal end (not shown) inserted through the stylet access port of the housing 22 and into the lumen of the pacing lead 24. The stylet 26 can be used to guide the pacing lead 24 to the pacing site in the patient's heart.

The power pull-tab 28 extends into the housing 22 and insulates the battery from the pacing electronics while in storage mode. This extends the shelf life of the pacemaker system 20. The power pull-tab 28 is pulled out of or removed from the housing 22 to use the pacemaker system 20 in pacing mode. In embodiments, removing the power pull-tab 28 starts the PG 21, such that the PG 21 generates electrical pulses that are delivered to the pacing electrodes 34 and 36.

In embodiments described below, the housing 22 includes two body portions, which may be referred to as halves. The pacing lead 24 is secured to a first body portion and the PG assembly, such as PG printed circuit board assembly 48, that includes the one or more pulse generator contacts and the pacing electronics and the battery is situated in and sealed into a second body portion. The one or more pulse generator contacts, which are coupled to the pacing electronics, are electrically coupled to the one or more pacing lead contacts of the pacing lead 24 through a compression fit of the first and second portions of the housing 22.

In use, the distal end of the stylet 26 is inserted through the stylet access port of the housing 22 and into the lumen of the pacing lead 24. The pacing electrodes 34 and 36 of the pacing lead 24 are guided to the pacing site in the patient's heart using the stylet 26 and the power pull-tab 28 is removed to start the PG 21 pulsing, which provides electrical pulses to the pacing electrodes 34 and 36.

Figure 2:
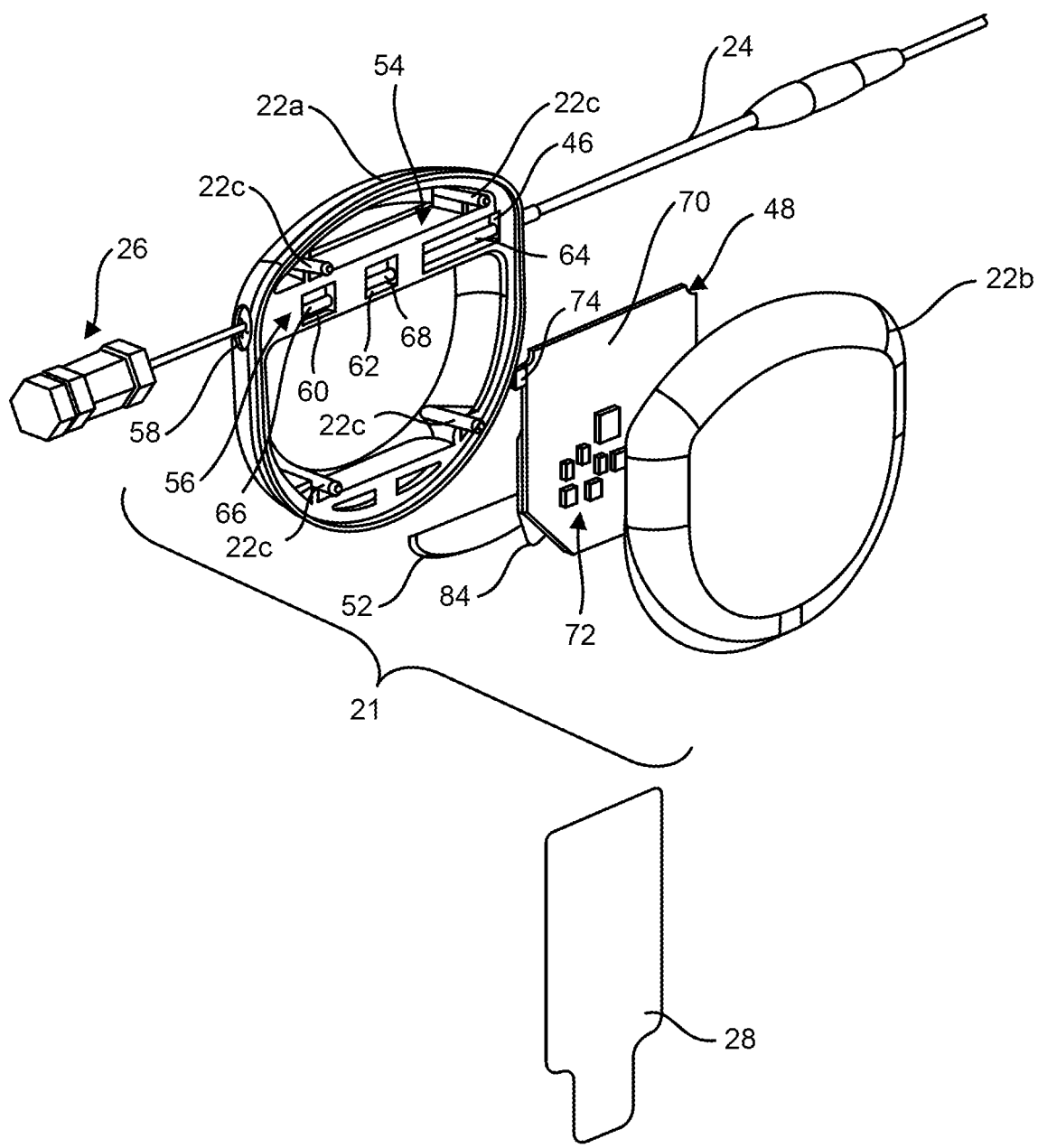
FIG. 2 is a diagram illustrating a partially exploded view of the disposable temporary pacemaker system from one side of the pacemaker system, according to embodiments of the disclosure.
Figure 3:
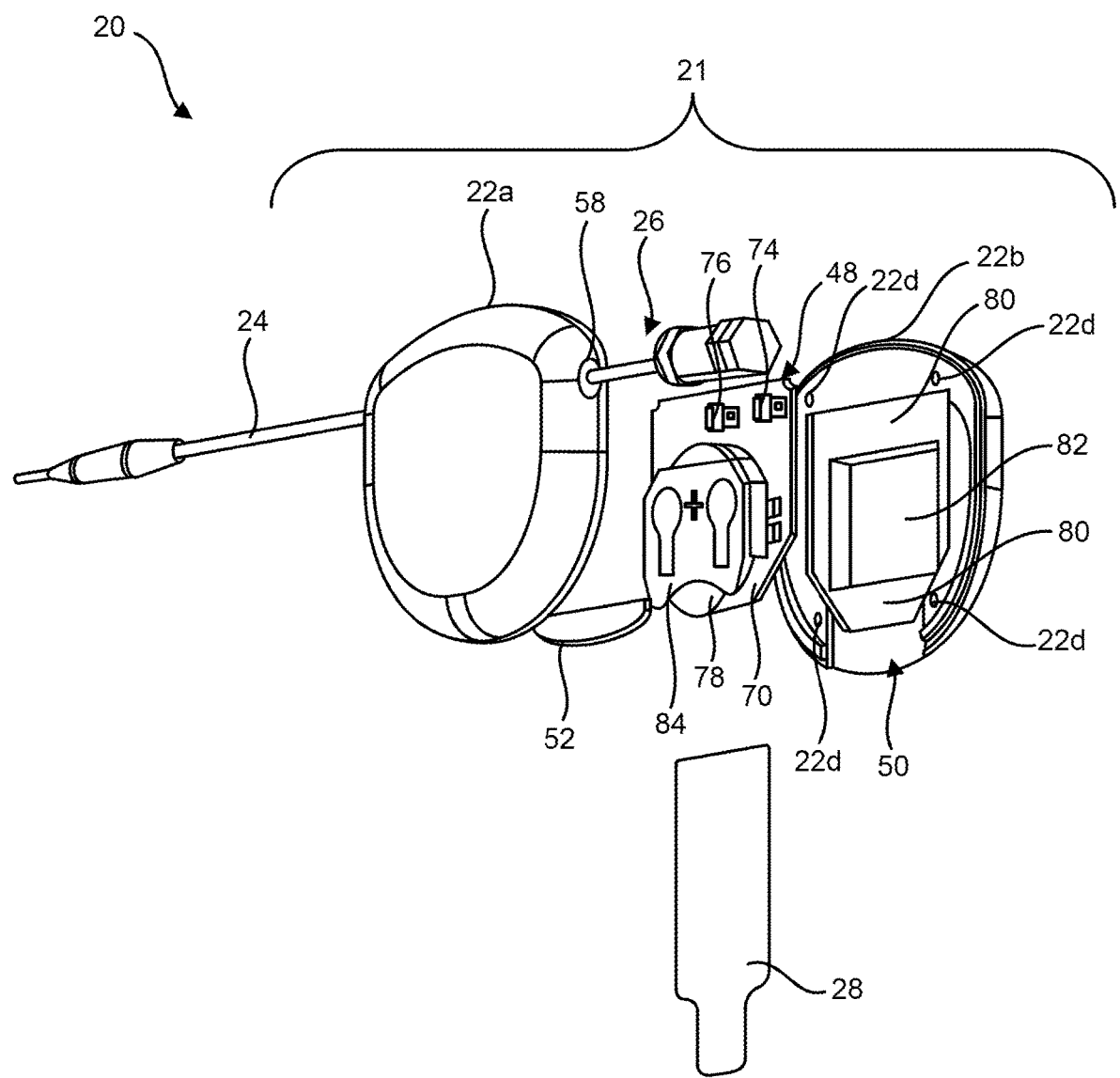
FIG. 3 is a diagram illustrating a partially exploded view of the disposable temporary pacemaker system from the other side of the pacemaker system, according to embodiments of the disclosure.

FIGS. 2 and 3 are diagrams illustrating partially exploded views of the disposable temporary pacemaker system 20, according to embodiments of the disclosure, where the disposable temporary pacemaker system 20 includes the PG 21, the pacing lead 24, the stylet 26, and the power pull-tab 28.

FIG. 2 is a diagram illustrating a partially exploded view of the disposable temporary pacemaker system 20 from one side of the pacemaker system 20, according to embodiments of the disclosure. FIG. 3 is a diagram illustrating a partially exploded view of the disposable temporary pacemaker system 20 from the other side of the pacemaker system 20, according to embodiments of the disclosure.

The housing 22 includes a first portion 22a and a second portion 22b that are fit together to form the housing 22. The first portion 22a can be permanently or irremovably, physically secured to the pacing lead 24. The second portion 22b is attached to the PG printed circuit board assembly 48. In embodiments, the first portion 22a and the second portion 22b are compression fit together to form the housing 22. In embodiments, the first portion 22a and the second portion 22b include friction-fit pins 22c and holes 22d that when compressed together create a mechanical bond between the first and second portions 22a and 22b. In embodiments, the friction fit pins 22c are hexagonal and the holes 22d are round. In embodiments, the first and second portions 22a and 22b may be fit together using adhesives or the bond between them may be enhanced using adhesives. In embodiments, the first portion 22a and the second portion 22b may be fit together in another way, such as with latches or snap fit together, to form the housing 22.

The second portion 22b of the housing 22 includes a slot 50 that the power pull-tab 28 resides in and the first portion 22a has a flexible, expandable piece of material 52 situated on or attached to the first portion 22a, which corresponds to the slot 50. The piece of material 52 expands into the slot 50 to restrict ingress of moisture into the housing 22 after the power pull-tab 28 has been removed.

Figure 4A:
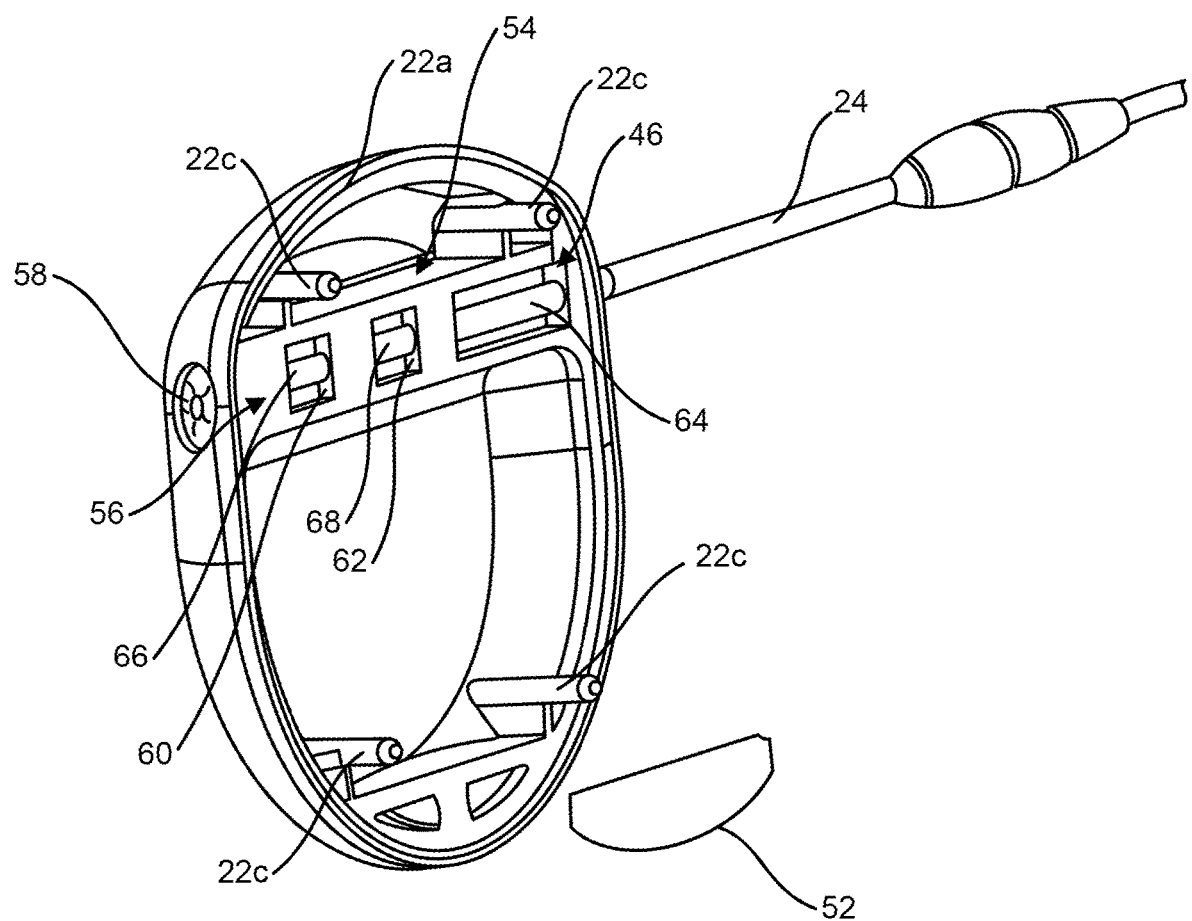
FIG. 4A is a diagram illustrating an expandable piece of material separated from the first portion of the housing, according to embodiments of the disclosure.
Figure 4B:
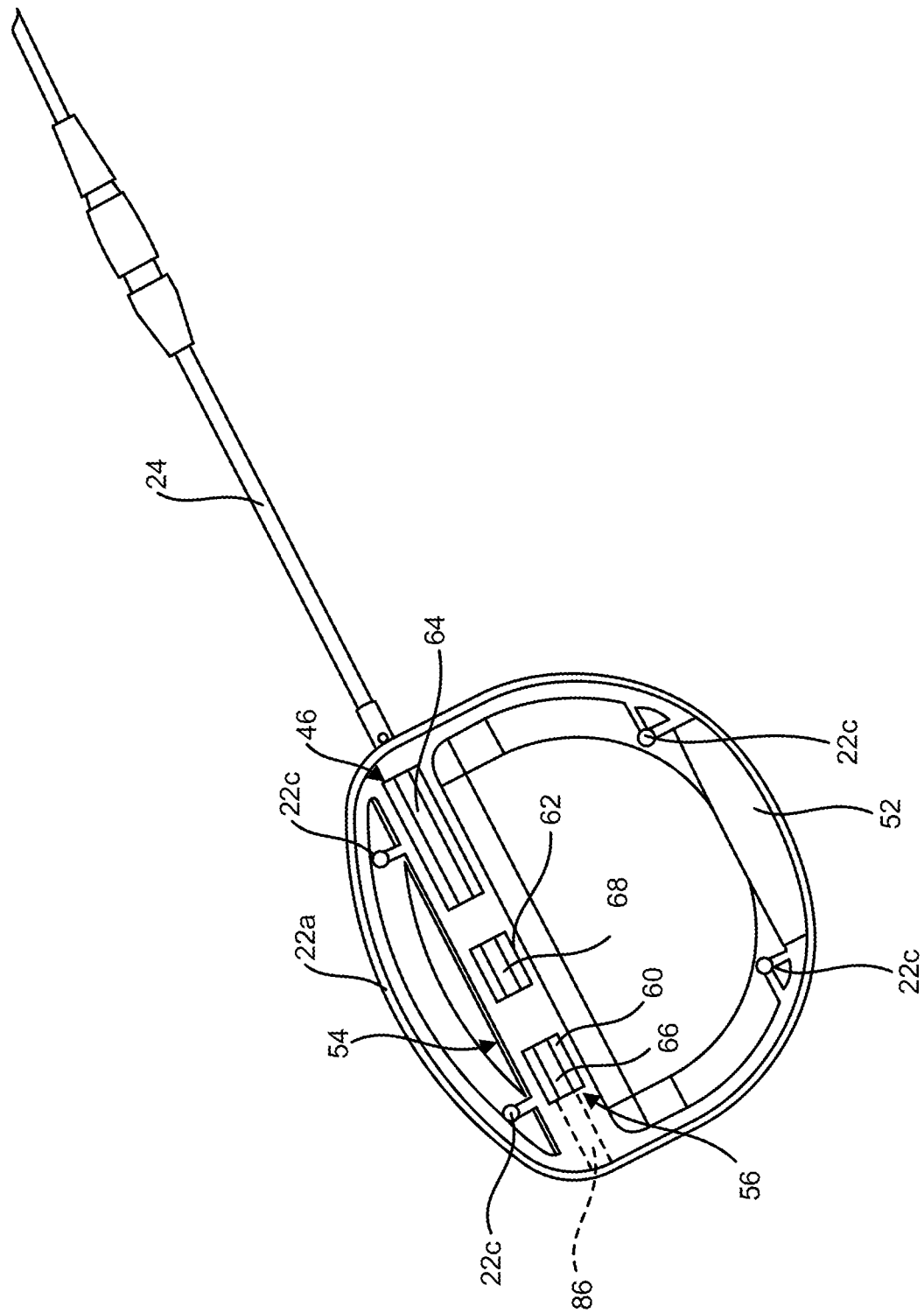
FIG. 4B is a diagram illustrating the piece of material on or attached to the first portion of the housing, according to embodiments of the disclosure.

The first portion 22a and the piece of material 52 are further illustrated in FIGS. 4A and 4B. FIG. 4A is a diagram illustrating the piece of material 52 separated from the first portion 22a, according to embodiments of the disclosure. FIG. 4B is a diagram illustrating the piece of material 52 on or attached to the first portion 22a, according to embodiments of the disclosure. In embodiments, the piece of material 52 can be attached to the first portion 22a with an adhesive or any other suitable attachment means.

In reference to FIGS. 1-4, the first portion 22a includes a channel structure 54 configured to receive the proximal end 56 of the pacing lead 24. In embodiments, the channel structure 54 includes a tight tolerance channel that receives part of the pacing lead 24 and the proximal end 56 of the pacing lead 24.

The channel structure 54 is used to register the proximal end 56 of the pacing lead 24 with the stylet access port 58 of the first portion 22a. The stylet access port 58 includes a hole or passageway 86, indicated in dashed lines in FIG. 4B, that extends through the first portion 22a of the housing 22 and into the channel of the channel structure 54. To ease insertion and reinsertion of the stylet 26 into the housing 22 and the pacing lead 24, the stylet access port 58 includes a conical divot. The stylet access port 58 is used to insert and guide the stylet 26 through the passageway 86 of the first portion 22a of the housing 22 and into the lumen of the pacing lead 24. In embodiments, the stylet 26 may be extended to the distal end of the pacing lead 24 and is used to implant the pacing lead 24 in the patient. In embodiments, the stylet 26 is removed once the pacing lead 24 is positioned in the patient as desired by the clinician. However, the construction of the pacemaker system 20 allows the user to re-insert the stylet 26 into the housing 22 and the pacing lead 24 after initial delivery of the pacing lead 24. For example, situations may arise in which the clinician desires to reposition the pacing electrodes 34, 36 based on pacing thresholds, e.g., where such thresholds change during use. The design of the housing 22 and the pacing lead 24 provide the clinician with significant flexibility to tailor the use of the pacemaker system 20 based on the particular clinical needs.

The first portion 22a includes openings or windows into the channel structure 54, including a first contact window 60, a second contact window 62, and a pacing lead window 64. The first and second contact windows 60 and 62 are for making electrical contact between the pacing lead 24 and the PG printed circuit board assembly 48. The pacing lead window 64 forms a moat in the channel structure 54 that is used for securing the pacing lead 24 in the first portion 22a. In embodiments, the moat of the pacing lead window 64 is filled with epoxy or adhesive 46 that adheres to the pacing lead 24 and prevents the pacing lead 24 from becoming dislodged form the first portion 22a.

The pacing lead 24 is inserted into the channel structure 54 of the first portion 22a. The pacing lead 24 includes a first pacing lead contact 66 that is aligned with the first contact window 60 and a second pacing lead contact 68 that is aligned with the second contact window 62. The first and second pacing lead contacts 66 and 68 electrically couple the pacing lead 24 to the PG printed circuit board assembly 48 through the first and second contact windows 60 and 62.

A portion of the pacing lead 24 that is distal the second pacing lead contact 68 is aligned with the pacing lead window 64, and, in embodiments, the pacing lead 24 is permanently or irremovably, physically secured to the first portion 22a through the pacing lead window 64. However, as described elsewhere herein, in other embodiments the pacing lead 24 can be provided separate from the housing 22 and removably coupled to the housing 22 by the clinician prior to use.

In embodiments, the pacing lead 24 is secured to the first portion 22a through the pacing lead window 64 by using an adhesive 46 to attach or bond the pacing lead 24 to the first portion 22a. In embodiments, the pacing lead 24 is secured to the first portion 22a through the pacing lead window 64 by using epoxy to attach or bond the pacing lead 24 to the first portion 22a. In embodiments, the pacing lead 24 is secured to the first portion 22a through the pacing lead window 64, such as by crimping or inserting a clip to hold the pacing lead 24 in place in the first portion 22a.

Figure 5A:
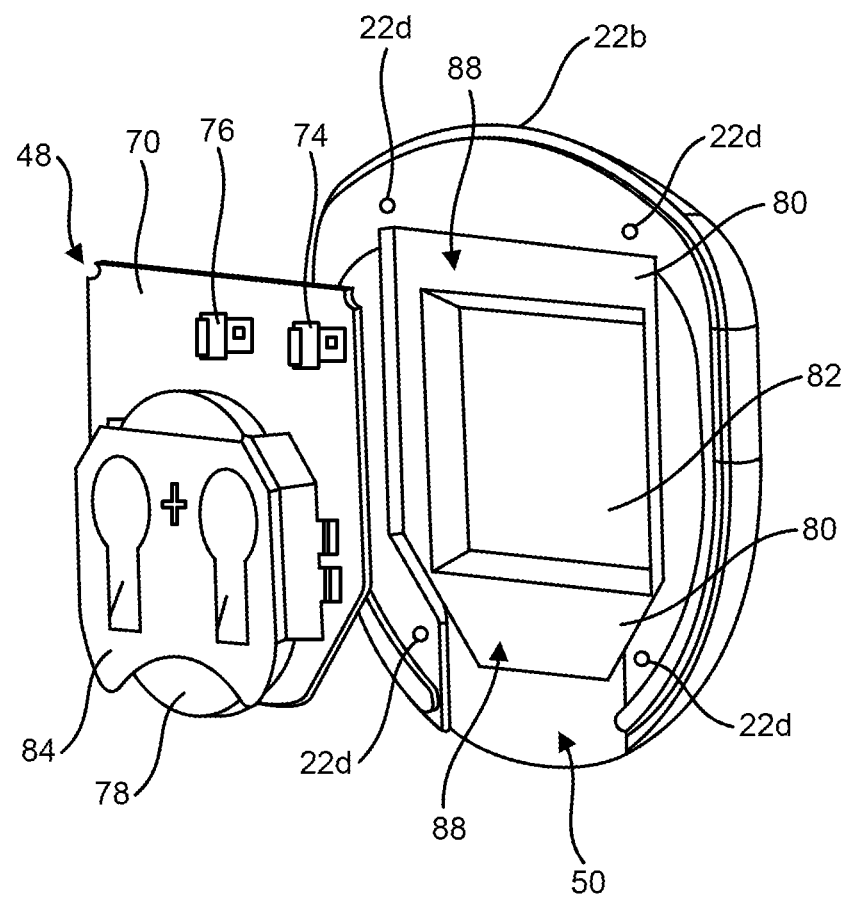
FIG. 5A is a diagram illustrating a pulse generator (PG) printed circuit board assembly separated from the second portion of the housing, according to embodiments of the disclosure.
Figure 5B:
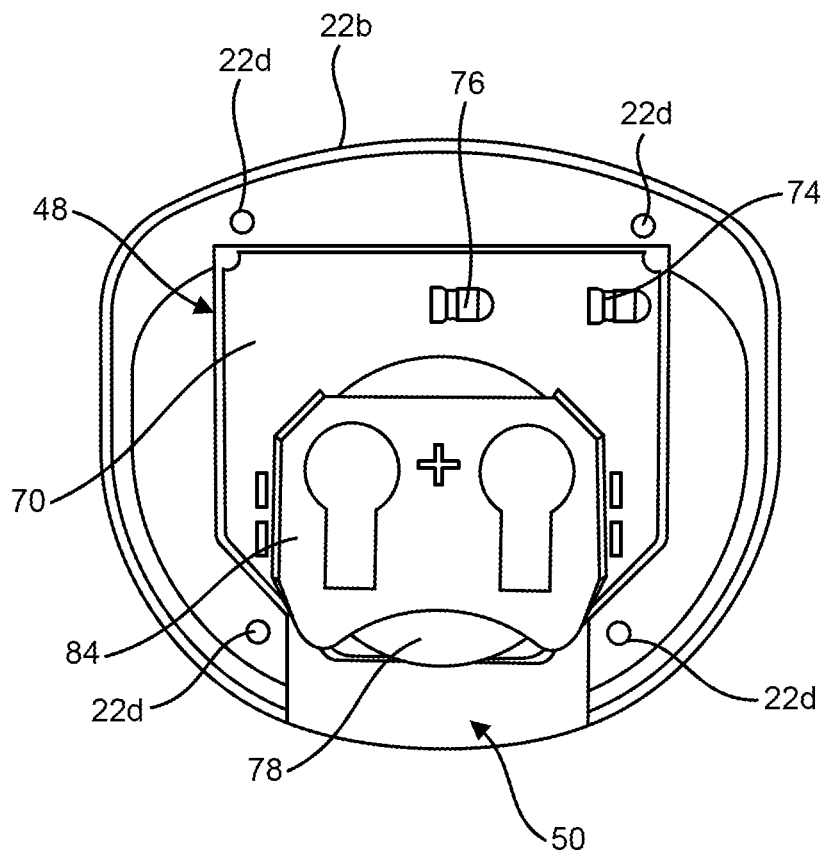
FIG. 5B is a diagram illustrating the PG printed circuit board assembly attached to the second portion of the housing, according to embodiments of the disclosure.

The second portion 22b and the PG printed circuit board assembly 48 are further illustrated in FIGS. 5A and 5B. FIG. 5A is a diagram illustrating the PG printed circuit board assembly 48 separated from the second portion 22b, according to embodiments of the disclosure. FIG. 5B is a diagram illustrating the PG printed circuit board assembly 48 attached to the second portion 22b, according to embodiments of the disclosure. In embodiments, the PG printed circuit board assembly 48 can be attached to the second portion 22b with an adhesive or sealant.

In reference to FIGS. 1-5B, the PG printed circuit board assembly 48 includes the printed circuit board 70 that includes the pacing electronics 72, such as a pacemaker chip set, on one side and the pulse generator contacts 74 and 76, battery 78, and battery holder 84 on the other side.

The pacing electronics 72 are electrically coupled to the pulse generator contacts 74 and 76 and configured to provide electrical pulses at the pulse generator contacts 74 and 76. In embodiments, the pacing electronics 72 includes registers that provide register control for pacing. In embodiments, the pacing electronics 72 includes registers that provide register control via state machines. In embodiments, the pacing electronics 72 can be programmed externally. In embodiments, the pacing electronics 72 provide therapy using preset factory settings. In embodiments, the settings of the pacing electronics 72 can be modified using a programmer after the pacing lead 24 has been implanted. In embodiments, the settings of the pacing electronics 72 can be modified using a programmer before implanting the pacing lead 24. In embodiments, the pacing electronics 72 can include a microprocessor to facilitate enhanced programming and communication capabilities.

When the first portion 22a and the second portion 22b are fit together, the pulse generator contacts 74 and 76 electrically couple the PG printed circuit board assembly 48 to the first and second pacing lead contacts 66 and 68, respectively, of the pacing lead 24 through the first and second contact windows 60 and 62, respectively. With the PG printed circuit board assembly 48 pulsing, this provides electrical pulses to the pacing electrodes 34 and 36 of the pacing lead 24 to pace the patient. In the illustrated embodiment, the pulse generator contacts 74 and 76 are electrical spring contacts. However, the present disclosure contemplates any type of electrical contact structure or technology for providing electrical continuity between the PG printed circuit board assembly 48 and the pacing electrodes 34 and 36.

The second portion 22b of the housing 22 includes a shelf 80 and a cavity 82 that can be made into a waterproof cavity to protect the pacing electronics 72 from moisture. The printed circuit board 70 is shaped to fit onto the shelf 80 of the second portion 22b with the pacing electronics 72 fitting into the cavity 82. Also, the shape of the shelf 80 and the cavity 82 provide alignment of the printed circuit board 70 within the housing 22, such that the PG printed circuit board assembly 48 fits into the housing 22 and electrical contacts align when compressing the first and second portions 22a and 22b together. This results in a PG 21 and housing 22 as shown in FIG. 1. In embodiments, a sealant and/or gasketing material 88, as shown in FIG. 5A, can be placed on the shelf 80 that surrounds the cavity 82 and/or around the pacing electronics 72 on the printed circuit board 70 to make the cavity 82 into a water-tight pocket or cavity 82 for the pacing electronics 72. In one embodiment, the sealant and/or gasketing material 88 may be made from or include a polymeric or elastomeric material, e.g., silicone. However, the particular material used to form the gasketing material 88 is not critical to the present disclosure, and any number of materials may be used within the scope of the present disclosure.

The pulse generator contacts 74 and 76, the battery 78, and the battery holder 84 are on the side of the printed circuit board 70 that is opposite the pacing electronics 72. The battery holder 84 is configured to hold the battery 78 and, in embodiments, the battery holder 84 is a standard device that holds a commercially available battery.

In storage mode, the power pull-tab 28 is situated between the printed circuit board 70 and the battery 78 to insulate the battery 78 from the pacing electronics 72. The battery 78 is electrically coupled to the pacing electronics 72 when the power pull-tab 28 is removed from between the printed circuit board 70 and the battery 78. In some embodiments, this immediately powers the pacing electronics 72 and the PG 21 starts pulsing, which immediately commences therapy.

As stated in the previous paragraph, the illustrated embodiment uses the power pull-tab 28 to electrically isolate the battery 78 from the pacing electronics 72 prior to use of the pacemaker system 20 to delivery pacing pulses to the patient, so as to conserve battery power and inhibit unintended delivery of pacing pulses. However, the present disclosure is not limited to the particular illustrated battery isolation means, and the skilled artisan will readily recognize that other electrical isolation technologies can be employed to accomplish this function. In one such exemplary embodiment, a user-accessible switch can be provided to allow the clinician to switch the pacemaker system 20 from a first state in which the battery 78 is electrically isolated from the pacemaker electronics 72, to a second (e.g., ready) state in which the battery 78 is electrically coupled to the pacing electronics 72 so that the pacemaker system 20 can be used to deliver pacing stimuli to the patient as desired.

In embodiments, the pacing electronics 72 is configured to provide industry standard pacing modes, e.g., rate-adaptive pacing and anti-tachycardia pacing. In embodiments, the pacing electronics 72 can be used in pacing in a wide range of cardiac procedures, e.g., interventional cardiology and TAVR procedures. The pacemaker system 20 can be particularly useful for emergency procedures, e.g., emergency interventional cardiology procedures such as PTCA and stent implantation procedures, that often require temporary pacing. Unlike current temporary or permanent pacemaker systems on the market, the pre-packaged nature of the pacemaker system 20 components, and the simplified activation of the PG 21 can significantly shorten the amount of time required to begin pacing under these emergency conditions, e.g., by eliminating the need for a pre-operative electrophysiology study on the patient. Moreover, the pacing lead 24 of the pacemaker system 20 can be deployed exclusively under the imaging modalities already being used in the interventional cardiology procedure.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

The invention claimed is:

1. A disposable pacemaker, comprising:
a housing formed of a polymeric material;
a battery disposed within the housing;
a pulse generator circuit board assembly situated in the housing and including pacing electronics;
a power pull-tab removably configured to selectively electrically isolate the battery and the pacing electronics;
an expandable tab adapted to expand upon removal of the power pull-tab; and
a pacing lead that is irremovably secured to the housing and includes first and second electrodes each electrically coupled to the pulse generator circuit board assembly and configured to deliver pacing pulses generated by the pulse generator circuit board assembly.

2. The disposable pacemaker of claim 1, wherein the housing includes a first portion and a second portion secured together to form the housing.

3. The disposable pacemaker of claim 2, wherein the first portion and the second portion are secured together by at least one of an interference fit, an adhesive, or latches.

4. The disposable pacemaker of claim 2, wherein the pacing lead is irremovably secured to the first portion of the housing.

5. The disposable pacemaker of claim 2, wherein the pulse generator printed circuit board assembly includes electronics that face the second portion, and the pulse generator printed circuit board assembly and the second portion are sealed together to protect the electronics from an external environment.

6. The disposable pacemaker of claim 2, wherein the first portion includes a stylet port and the pacing lead includes a lumen aligned with the stylet port, such that the stylet port and the lumen of the pacing lead are configured to receive a stylet.

7. The disposable pacemaker of claim 1, wherein:
the pulse generator printed circuit board assembly includes a first pulse generator contact and a second pulse generator contact; and
the pacing lead includes a first pacing lead contact electrically coupled to the first electrode and to the first pulse generator contact, and a second pacing lead contact electrically coupled to the second electrode and the second pulse generator contact.

8. A disposable pacemaker comprising:
a housing including a first portion having a stylet port and a second portion;
a pulse generator printed circuit board assembly situated between the first portion and the second portion and including a battery, at least a first pulse generator contact and a second pulse generator contact, wherein the battery is secured onto the pulse generator printed circuit board, such that a power pull-tab is removably situated between the battery and the pulse generator printed circuit board to selectively electrically isolate the battery from the pulse generator printed circuit board; and
a pacing lead secured into the first portion, wherein the pacing lead has a first pacing lead contact electrically coupled with the first pulse generator contact, and a second pacing lead contact electrically coupled with the second pulse generator contact, the pacing lead further including a lumen aligned with the stylet port.

9. The disposable pacemaker of claim 8, wherein the stylet port and the lumen of the pacing lead are configured to receive a stylet.

10. The disposable pacemaker of claim 8, wherein the first portion and the second portion are secured together by at least one of an interference fit, an adhesive, or one or more latches.

11. The disposable pacemaker of claim 8, wherein the pulse generator printed circuit board assembly includes a circuit board and pacing electronics on the circuit board that face the second portion and comprising a seal formed between or around the circuit board and the second portion.

12. The disposable pacemaker of claim 8, wherein the pacing lead is permanently secured to the first portion of the housing.

13. A pacemaker kit comprising:
a disposable pacemaker including:
a housing having a stylet port;
a pulse generator printed circuit board assembly situated in the housing and including pacing electronics attached to a circuit board and a battery held on the circuit board; and
a pacing lead secured to the housing and including a lumen aligned with the stylet port, the pacing lead in electrical contact with the pacing electronics;
a stylet configured to be inserted into the stylet port and the lumen of the pacing lead; and
a power pull-tab removably positioned between the battery and the circuit board to electrically isolate the battery from the circuit board, wherein removal of the power pull-tab electrically couples the battery and the circuit board to enable the pulse generator printed circuit board assembly to generate electrical pacing pulses; and an expandable pad situated between the housing and the power pull-tab, wherein the expandable pad is adapted to expand upon removal of the power pull-tab.

14. The pacemaker kit of claim 13, wherein the housing includes a first portion and a second portion secured together to form the housing.

15. The pacemaker kit of claim 14, wherein the pacing lead is irremovably secured to the first portion.

16. The pacemaker kit of claim 14, wherein the circuit board is situated in the second portion with the pacing electronics facing the second portion and comprising a seal formed between or around the circuit board and the second portion to protect the pacing electronics from an external environment.

17. The pacemaker kit of claim 13, wherein the expandable pad expands to protect the inside of the housing upon removal of the power pull-tab from between the battery and the circuit board.

* * * * *